United States Patent
Marquette

[11] Patent Number: 6,153,139
[45] Date of Patent: Nov. 28, 2000

[54] PROSTHESIS COVERING APPARATUS

[76] Inventor: Stuart Marquette, 335 LaCosta Ave., Encinitas, Calif. 92121

[21] Appl. No.: 09/152,910

[22] Filed: Sep. 14, 1998

[51] Int. Cl.[7] .............................. B29C 33/40; A61F 2/50
[52] U.S. Cl. .................................. 264/219; 264/DIG. 30; 264/233; 425/2; 623/29; 623/54
[58] Field of Search .......................... 264/223, DIG. 30, 264/219; 425/2; 623/29, 54

[56] References Cited

U.S. PATENT DOCUMENTS

| | | |
|---|---|---|
| 2,666,208 | 1/1954 | Funk . |
| 2,684,487 | 7/1954 | Hansen . |
| 3,400,408 | 9/1968 | Garcia . |
| 3,501,777 | 3/1970 | Degtyarer et al. . |
| 3,953,900 | 5/1976 | Thompson . |
| 4,180,872 | 1/1980 | Chaikin . |
| 4,445,234 | 5/1984 | Ogunro ............................................. 3/1 |
| 4,735,754 | 4/1988 | Buckner ................................. 264/40.1 |
| 5,064,438 | 11/1991 | Nacder . |
| 5,133,775 | 7/1992 | Chen . |
| 5,452,780 | 9/1995 | Matt et al. . |
| 5,593,453 | 1/1997 | Ahlert . |

*Primary Examiner*—Jan H. Silbaugh
*Assistant Examiner*—Suzanne E. McDowell
*Attorney, Agent, or Firm*—Haugen Law Firm PLLP

[57] ABSTRACT

A method of making an external protective and cosmetic covering for use on an endoskeletal or exoskeletal prosthesis, that has toes included in it. The skin is produced on a mold having toes cut into it. The mold is narrower and undersized in the actual foot prosthesis. The mold is modified to have toes cut into it with the definition of the toes greatly exaggerated to emphasize the normal contours and definitions of the natural nail and natural nail bed.

6 Claims, 9 Drawing Sheets

PROSTHESIS COVERING APPARATUS

BACKGROUND OF THE INVENTION

I. Field of the Invention

The present invention relates to prosthesis coverings and more particular to an external protective and cosmetic covering for an endoskeletal or exoskeletal prosthesis.

II. Related Art

Prosthetic devices, such as legs, have advanced from simple wooden legs to complex mechanisms providing appropriate articulation at the knee, ankle and/or foot joints. These advances focus on facilitating a more natural gait for the prosthesis wearer which will reduce pressure on the wearer's body and reduce the wear and tear on the leg and its joint mechanisms. An example of a recent prosthetic device with a complex joint mechanism is disclosed in U.S. Pat. No. 5,425,780 to Flatt et al.

Prosthesis coverings serve two purposes. First, they provide an authentic leg look by incorporating skin color and texture. Second, these coverings protect the prosthesis and its mechanisms from the environment, increasing the life of the prosthesis. The coverings are either a part of the prosthesis or are separate. The separate coverings are often in the form of a sock that may have an open foot end or a closed foot end. Thus, the covering preferably has a skin tone and texture close to the wearer's skin in addition to accommodating repetitive movement at the ankle, knee and foot joints without creating excessive wrinkling or wear and tear at those locations.

One way to make the prosthesis look more realistic is to incorporate toes into the skin or foot. However, realistic looking toes are not easily made, especially on sock-type coverings. The assignee of the present invention, Daw Industries, has a sock-type covering with an open foot end. This covering is used on a prosthesis which may or may not have toes formed on the foot portion of the prosthesis. Thus, the prosthesis covering does not cover the toe portion of the foot. In order to have a realistic and complete appearance, Daw Industries provides a color coating for matching the toe end of the foot portion to the color of the prosthesis covering.

Therefore, what is needed is a closed end realistic-looking sock-type covering for a prosthesis device that has a realistic appearance of toes.

SUMMARY OF THE INVENTION

The present invention is a prosthesis covering that includes toes and a method for making the prosthesis covering. The covering is formed on a mold having a foot section incorporating toes. The depth and curvature between each toe is greater on the mold than that on a average foot or prosthesis, creating a highly exaggerated appearance of toes on the mold. The toenails and toenail beds are defined by lowering them in height from the upper surface of the foot section in a first embodiment. In a second embodiment, the grooves between the nail and the bed are increased. The foot mold is also undersized and narrower, preferably by 5–20%, than the actual foot prosthesis to be covered. The mold is then used to form the coverings.

The covering is intended to be put on in the manner of a sock and when stretched over the prosthetic foot section, which is larger in size than the covering, the toes expand to fit the particular prosthetic foot and provides a normal appearance of toes. The covering is secured with an adhesive that may or may not be removed.

BRIEF DESCRIPTION OF THE DRAWINGS

The foregoing features of the invention will become more readily apparent by referring to the following detailed description of the preferred embodiment, taken in conjunction with the accompanying drawings, in which.

DETAILED DESCRIPTION

Figure 1:
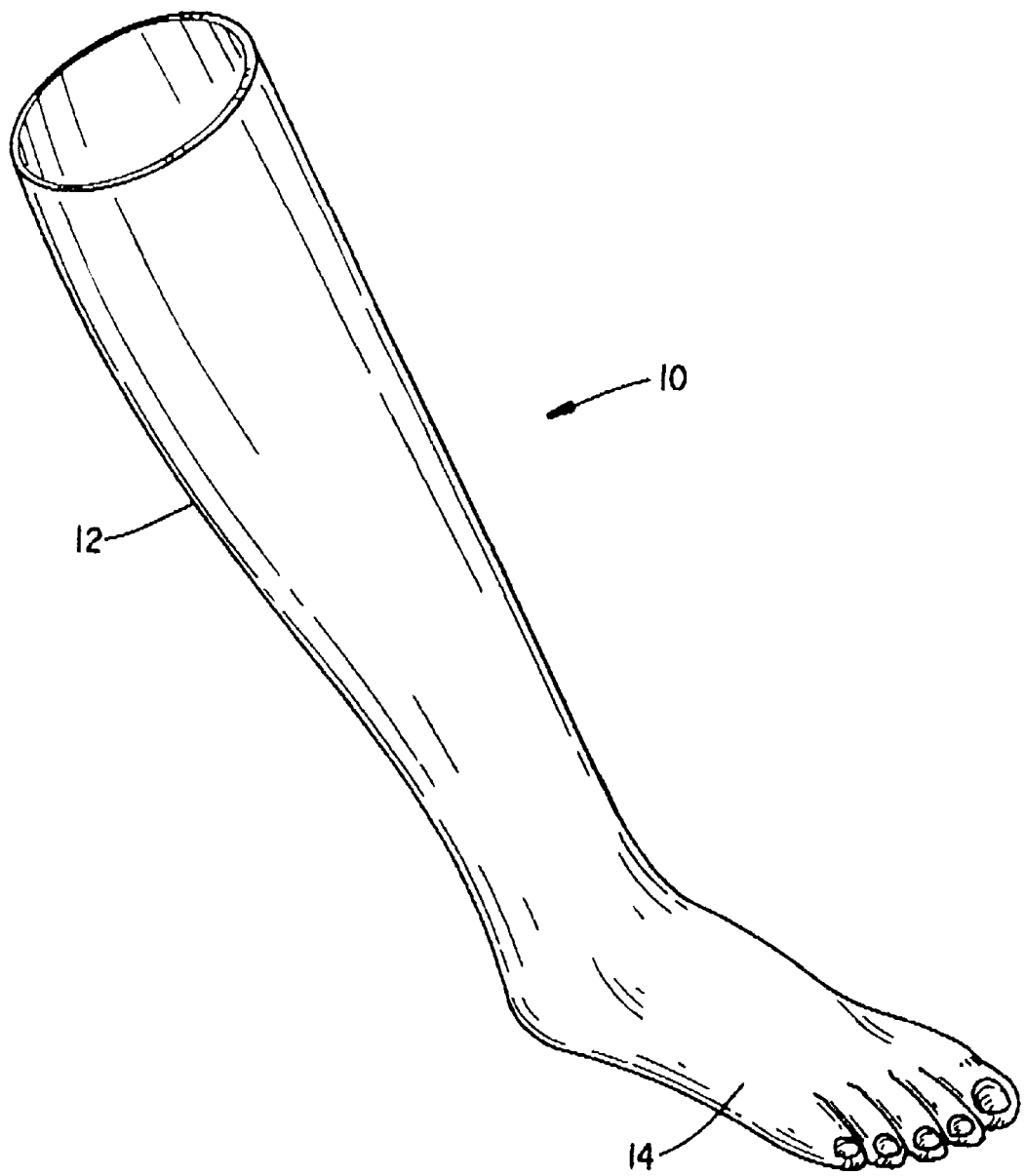
FIG. 1 is a perspective view of the prosthesis covering of the present invention.
Figure 2:
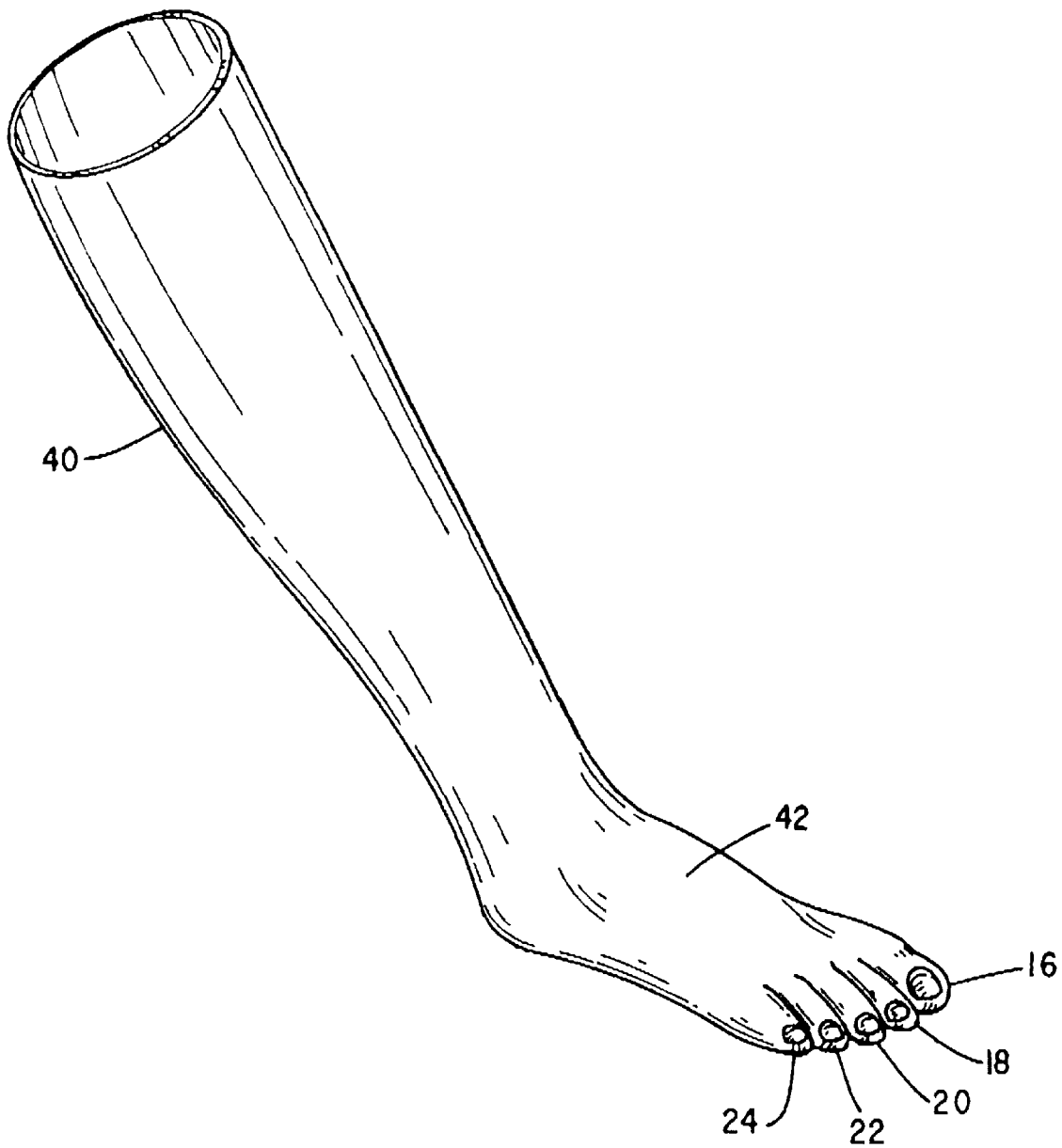
FIG. 2 is a perspective view of the mold used for making the prosthesis covering of the present invention.

The present invention is a prosthesis covering shown in FIG. 1 as 10, and a method of making the covering 10. The covering 10 includes a leg portion 12 which covers the leg section of a prosthesis (not shown) and a closed foot portion 14 which covers the foot of the prosthesis (not shown). Covering 10 is designed in the form of a stocking. The length of the leg portion 12 depends upon the size of the prosthesis which will be covered. The foot portion 14 includes indentations which form the appearance of toes. The foot portion 14 is narrower than the prosthetic foot, as will be explained in greater detail below. The prosthesis covering 10 is created by dipping a mold 40 (FIG. 2) into a suitable material which is then cured on the mold forming the prosthesis covering in a manner well known to those of skill in the art.

Figure 3:
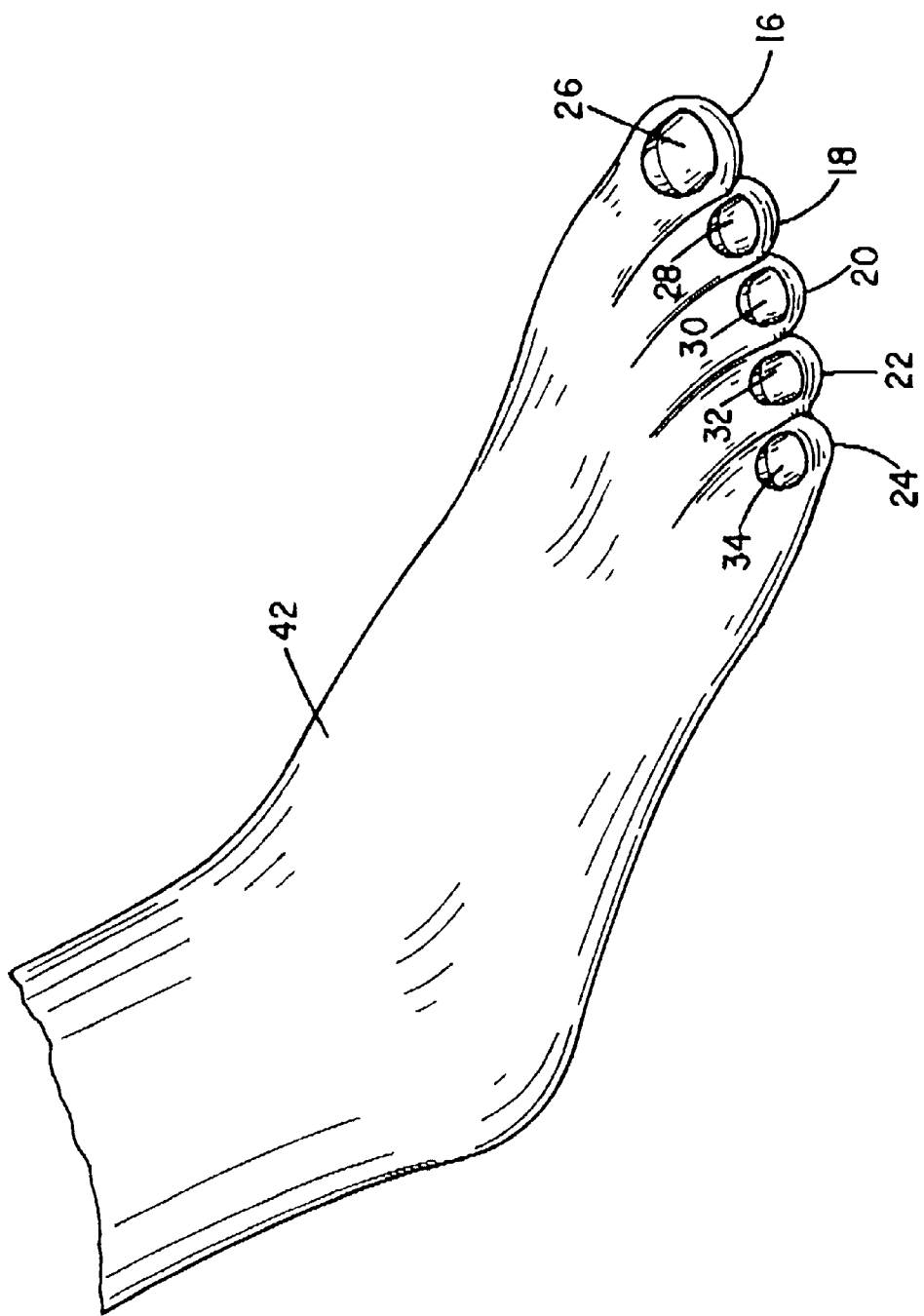
FIG. 3 is an enlarged portion of a foot section of the mold of FIG. 2.
Figure 4:
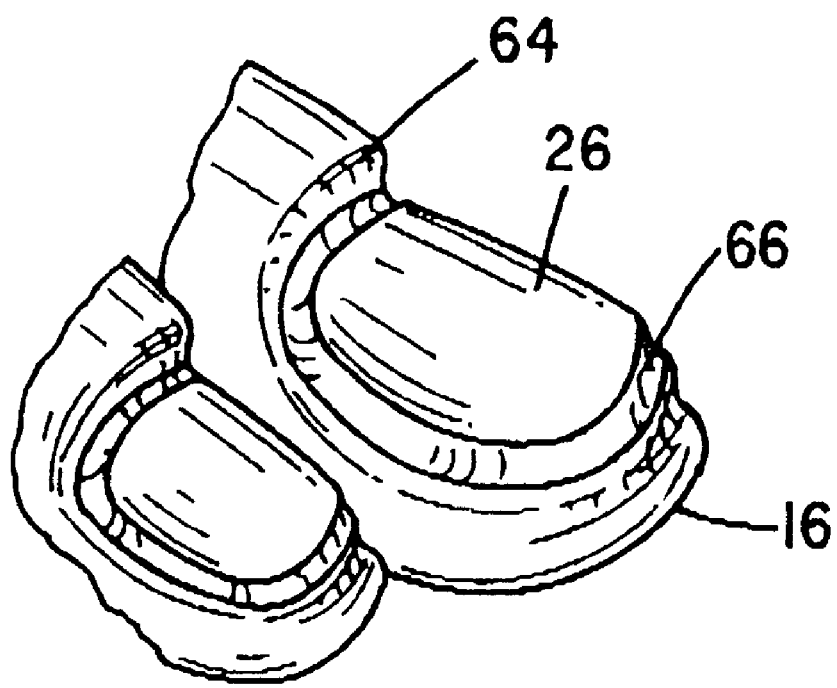
FIG. 4 is an enlarged portion of the big toe of the mold of FIG. 2.
Figure 5:
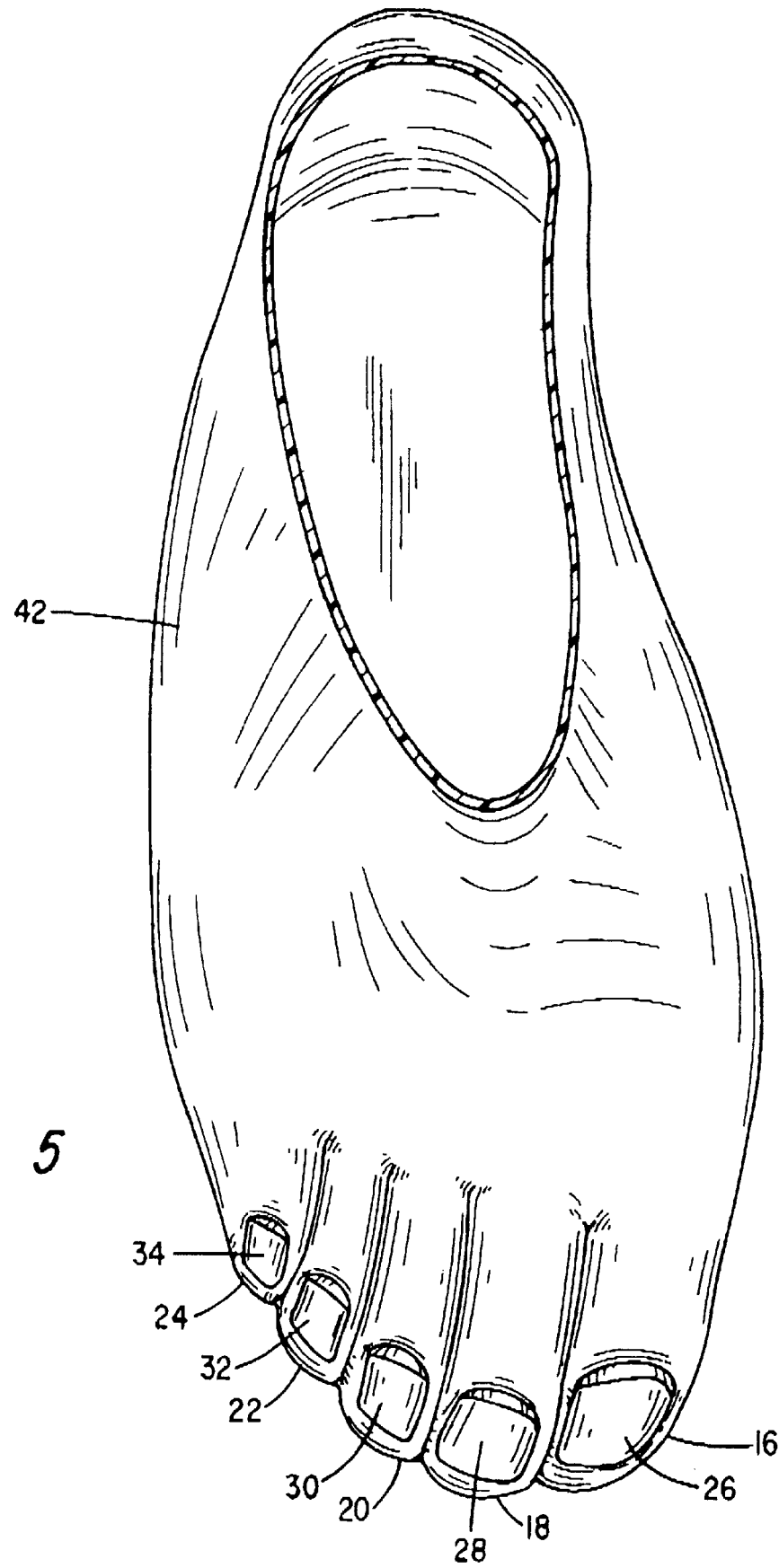
FIG. 5 is a top view of the foot section of the mold of FIG. 2.

Turning now to FIGS. 2–7, the foot section 42 of mold 40 will be described. Foot section 42 includes toes 16, 18, 20, 22 and 24 and toenails 26, 28, 30, 32 and 34 and is narrower and undersized than the actual foot component of the prosthesis to be covered. Five to twenty percent narrower is preferable depending upon the size of the prosthetic foot. Mold 40 is made from any standard mold material. Once it is cured and demolded, the foot section 42 of mold 40 is further altered to create exaggerated features of the toe area designated 44. The entire mold is laminated with an epoxy resin to create a master mold. The master mold is then duplicated with the toe section being solid resin. Toe definition is highly exaggerated As seen in FIGS. 3, 4 and 5, the big toe 16 has an inside arcuate surface 46 that has increased in depth, preferably by 0.060 inches to 0.180 inches and has a greater curvature than an average toe. Likewise, toe 18 adjacent to the big toe 16 has an increased depth on its inside arcuate surface 48 and greater curvature than an average toe and proportioned to the big toe 16. The arcuate surfaces 50, 52, 54, 56, 58 and 60 defining the remaining toes 20, 22 and 24 likewise have greater depth and curvature than an average toe, again proportioned to the curvature on the big toe 16.

Figure 9:
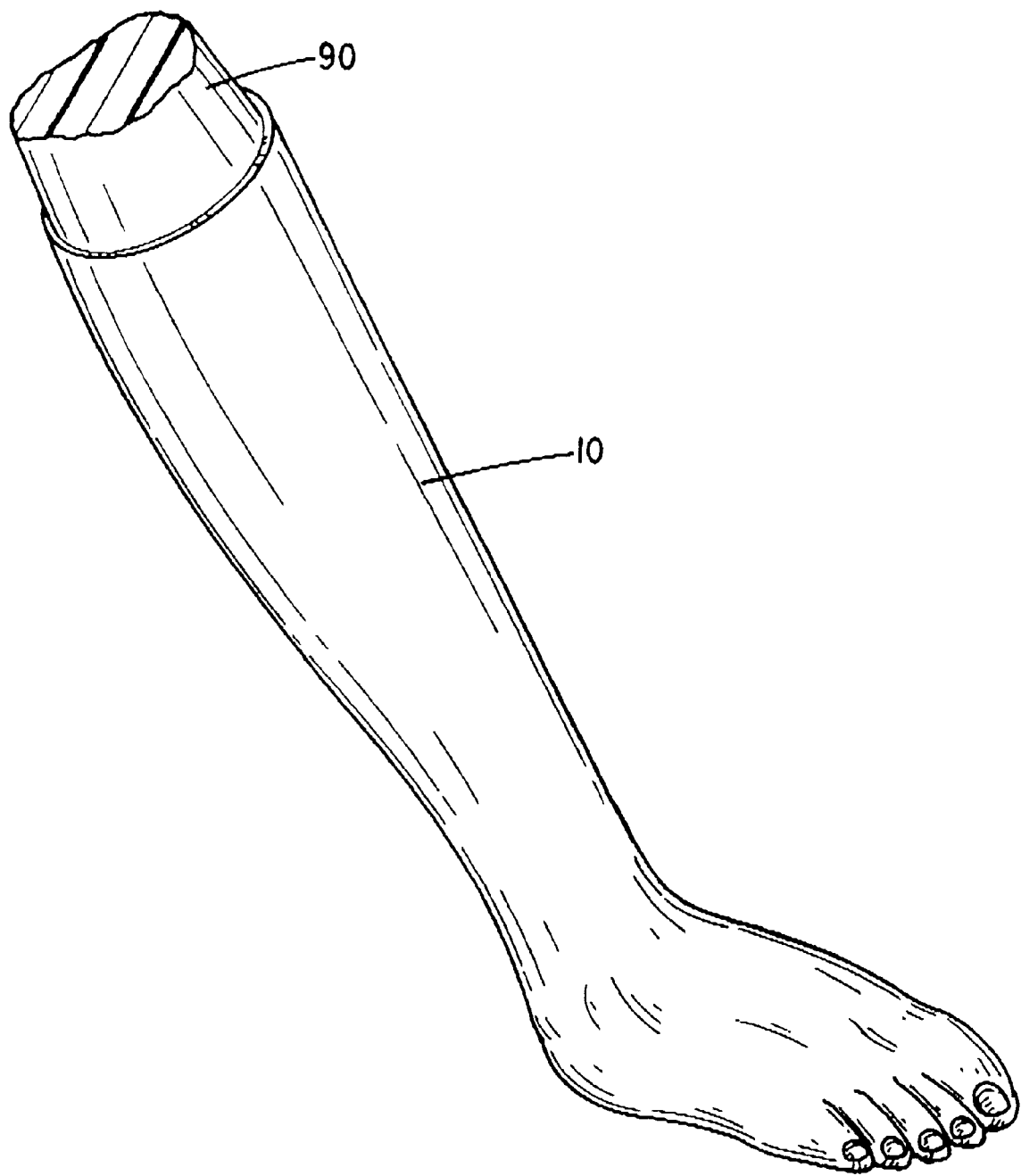
FIG. 9 is perspective view of the prosthesis covering of the present invention on a prosthesis.

The toenails 26, 28, 30, 32 and 34 are also greatly exaggerated on foot section 42. FIG. 4 shows an enlarged view of the big toe 16. Nail 26 is lowered, preferably by 0.060 inches to 0.180 inches, from the upper surface 64 of the foot section 42. Also, the definition around the toe nail 26 is increased by forming a surface 66 surrounding toe nail 26. The other nails are formed in the same manner with a lowered nail and surface surrounding the nail as shown in FIG. 3. The final mold 40 looks grossly deformed. However, when a covering 10 formed on this mold 40 is placed on a prosthesis, it no longer looks deformed, as seen in FIG. 9.

Figure 6:
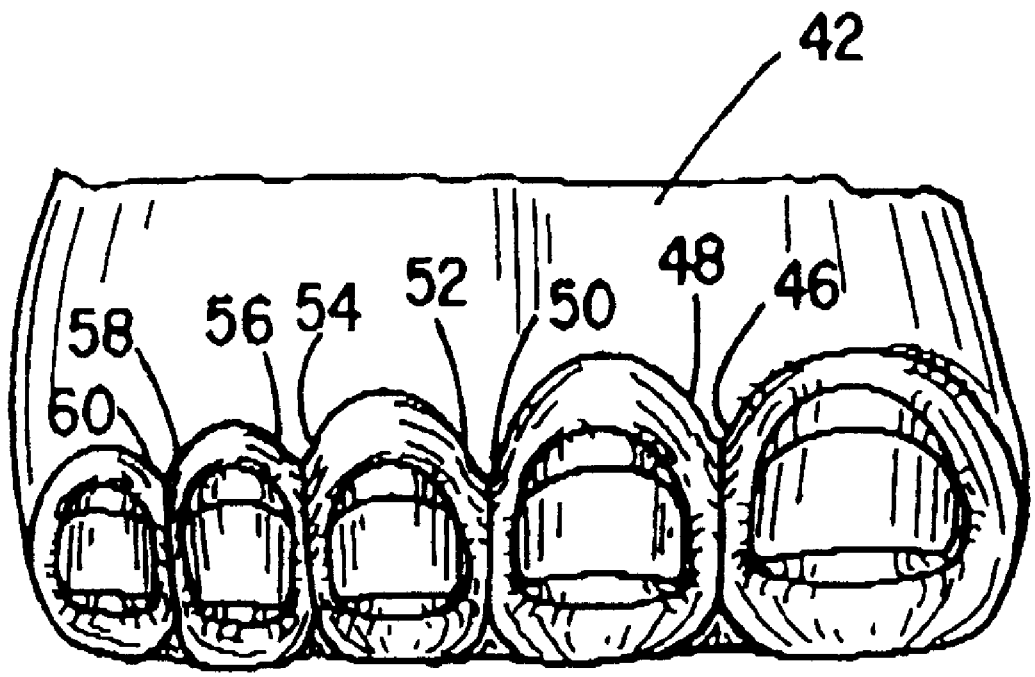
FIG. 6 is a side view of the foot mold used in forming the prosthesis covering of the present invention.
Figure 7:
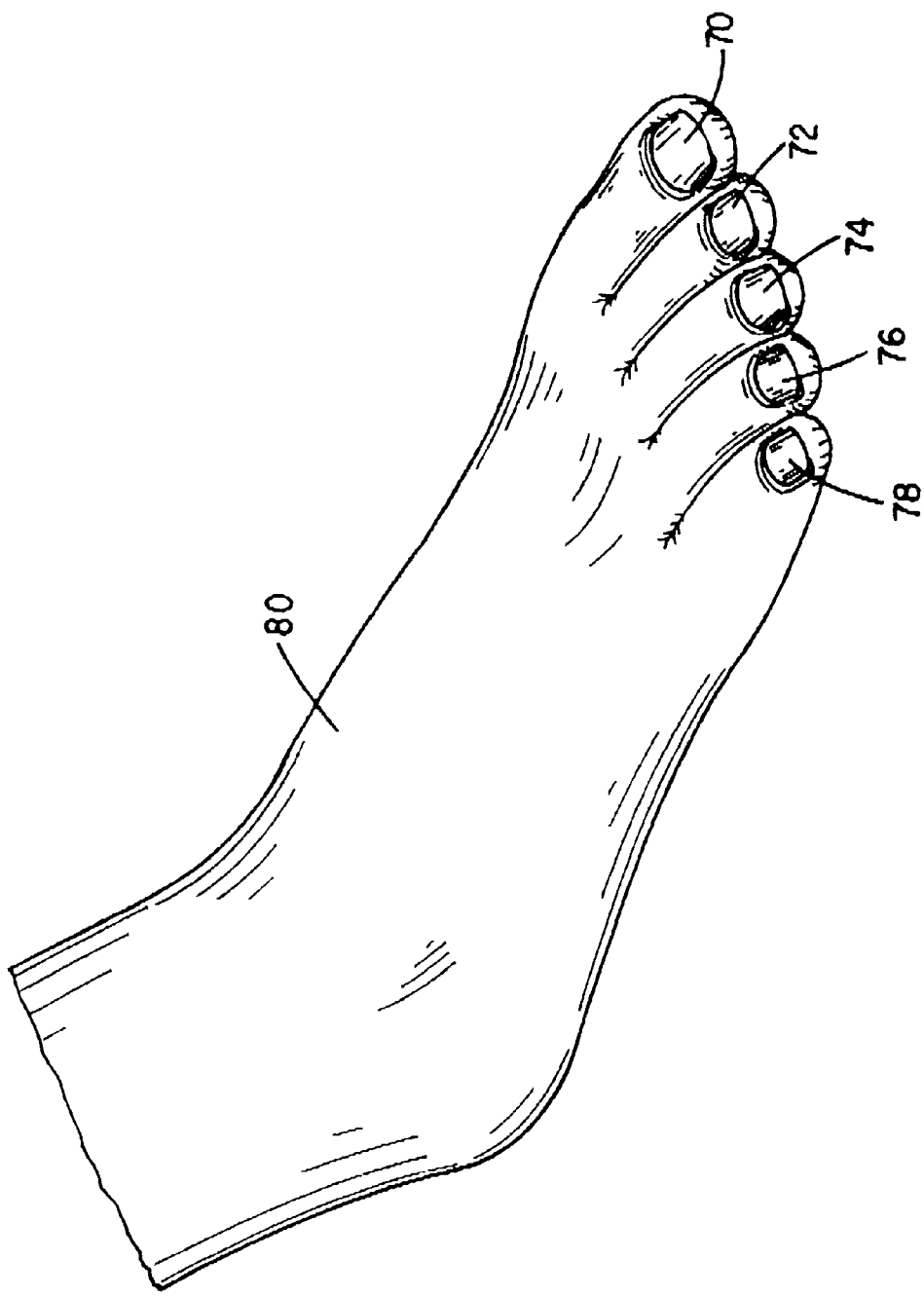
FIG. 7 is an enlarged portion of a foot section of a second embodiment the mold of FIG. 2.
Figure 8:
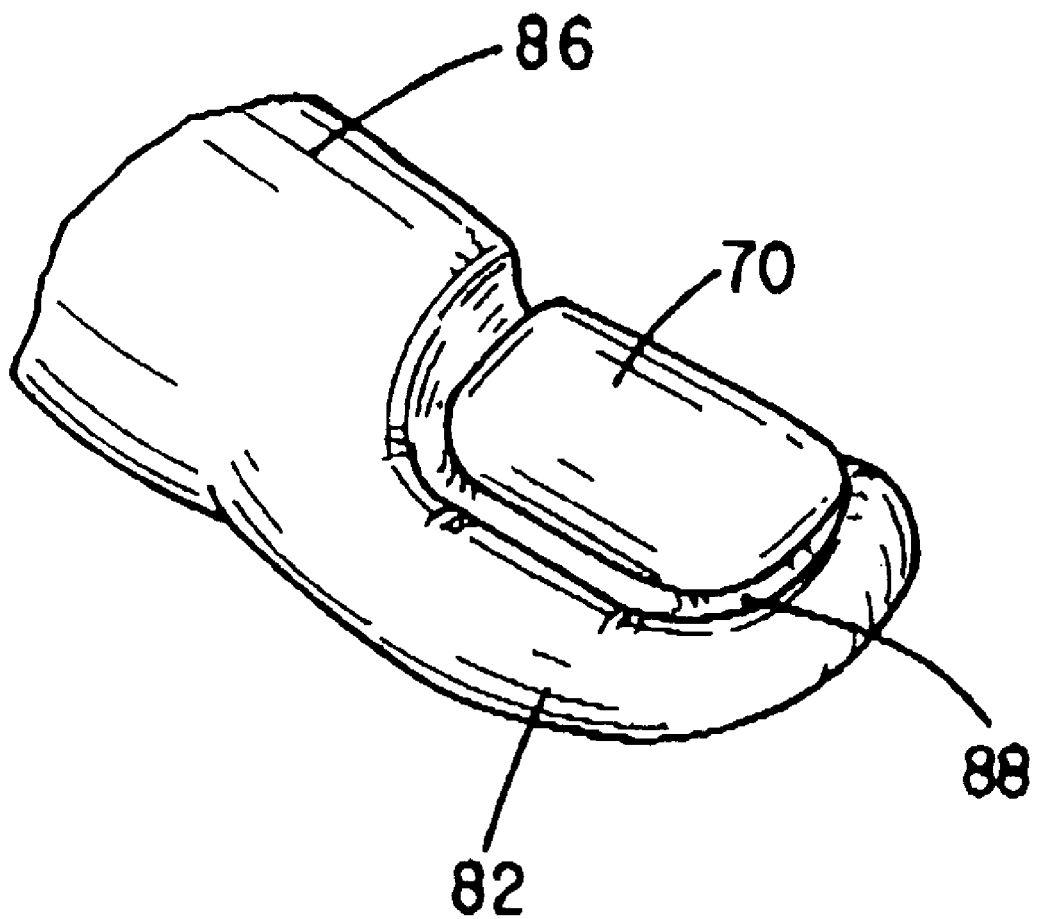
FIG. 8 is an enlarged portion of the big toe of the mold of FIG. 5.

A second toe nail embodiment is shown in FIGS. 7 and 8. The toenails 70, 72, 74, 76 and 78 are also greatly exaggerated on foot section 80. FIG. 6 shows an enlarged view of the big toe 82. Nail 70 is lowered slightly, preferably by 0.060 inches to 0.180 inches from the upper surface 86 of the foot section 80. Groove 88 between nail 70 and big toe 82 is increased in depth. This groove is preferably 0.120 inches to 0.280 inches. The other nails are formed in the same manner with a deep grove surrounding the nail as shown in FIG. 7. Again, while foot section 80 looks grossly deformed, when a covering 10 formed on it is placed on a prosthesis, it no longer looks deformed.

As explained above, the prosthesis covering mold is dipped in and sprayed with a suitable material, removed and then allowed to cure. Once cured, the prosthesis covering 10 is removed from the mold. The covering may then be put on the prosthesis 90 in the conventional manner, as in putting on a stocking, the material stretched over the heel and then stretched fully up the prosthesis leg above the socket brim. The foot prosthesis is larger than the foot portion of the skin and thus it stretches the skin over the foot, at the same time creating a natural appearance of toes as seen by FIG. 9. The covering may be applied with a glue for permanent use on the prosthesis or may be secured in a manner that allows it to be removed to allow repair to the prosthesis.

This invention has been described herein in considerable detail in order to comply with the Patent Statutes and to provide those skilled in the art with the information needed to apply the novel principles and to construct and use such specialized components as required. However, it is to be understood that the invention could be carried out by specifically different equipment and devices, and that various modifications, both as to the equipment details and operating procedures, can be accomplished without departing from the scope of the invention itself.

What is claimed is:

1. A method of making an external protective and cosmetic covering for use on an endoskeletal or exoskeletal prosthesis, said cover to be stretched over a prosthetic foot section, said method including the steps of a) molding a mold with a foot section, said foot section being undersized and narrower than said prosthesis foot section;

b) forming exaggerated toes, toenails, and nail beds on said foot section, wherein the depth and curvature between each toe on said foot section is greater than on an average foot and the height of said toenails and nail beds is lower than on an average toe;

c) dipping said mold with said foot section in skin material;

d) curing said skin material on said mold to form said covering; and e) removing said covering from said mold.

2. A method of claim 1 wherein said toenail and nail beds are lowered at least 0.060 inches.

3. A method of claim 1 wherein said toenail and nail beds are lowered approximately 0.060 inches to 0.180 inches.

4. A method of claim 1 wherein said forming said exaggerated toes imparting an aesthetically-pleasing normal toe appearance includes the step of increasing in depth the groove between the nail and the bed and around the distal border of the nail.

5. A method of claim 4 wherein said groove is increased in depth at least 0.120 inches.

6. A method of claim 4 wherein said groove is increased in depth approximately 0.120 inches to 0.280 inches.

\* \* \* \* \*